United States Patent [19]
Moroney, III et al.

[11] Patent Number: 5,993,611
[45] Date of Patent: Nov. 30, 1999

[54] CAPACITIVE DENATURATION OF NUCLEIC ACID

[75] Inventors: Richard Morgan Moroney, III, Plainsboro; Rajan Kumar, Robbinsville; Daniel Matt Fishman, Pennington, all of N.J.

[73] Assignee: Sarnoff Corporation, Princeton, N.J.

[21] Appl. No.: 08/936,323

[22] Filed: Sep. 24, 1997

[51] Int. Cl.⁶ .................................................. C12Q 01/68
[52] U.S. Cl. ............................ 204/157.6; 205/701; 435/6
[58] Field of Search ................................ 204/450, 157.6, 204/157.64, 157.67, 157.68; 435/173.1, 6, 91.1, 91.52; 205/701

[56] References Cited

U.S. PATENT DOCUMENTS

| | | |
|---|---|---|
| 5,244,787 | 9/1993 | Key et al. |
| 5,350,686 | 9/1994 | Jhingan. |
| 5,527,670 | 6/1996 | Stanley ........................................ 435/6 |
| 5,607,832 | 3/1997 | Stanley et al. .............................. 435/6 |
| 5,824,477 | 10/1998 | Stanley ........................................ 435/6 |
| 5,856,174 | 1/1999 | Lipshutz et al. ..................... 435/286.5 |

FOREIGN PATENT DOCUMENTS

| | | | |
|---|---|---|---|
| 2247889 | 3/1992 | United Kingdom ....................... 435/6 |
| WO 92/04470 | 3/1992 | WIPO ........................................ 435/6 |
| WO93/15224 | 8/1993 | WIPO. | |
| WO 95/25177 | 9/1995 | WIPO ........................................ 435/6 |

OTHER PUBLICATIONS

Stroop et al., "Comparative Effect of Microwaves and Boiling on the Denaturation of DNA," *Analytical Biochemistry*, 182:222–225, 1989.

L G Labrecque, "In situ hybridisation of EBV DNA–DNA hybrids using wet heat in polypropylene containers," *J. Clin. Pathol.*, 45:1099–1104, 1992.

Coates et al., "Rapid technique of DNA–DNA in situ hybrisation on formalin fixed tissue sections using microwave irradiation," *J. Clin. Pathol*, 40:865–869, 1987.

Hamrick et al., *Biosis Abstract No. 11432v*, 56(2):400–404, 1973.

Forster et al., *TIG*, 6(5):141, 1990.

*Primary Examiner*—Robert J. Warden, Sr.
*Assistant Examiner*—Andrew Aldag
*Attorney, Agent, or Firm*—William J. Burke

[57] ABSTRACT

The present invention relates to the denaturation of nucleic acids using capacitive charging. In a preferred embodiment, the invention effects such denaturation in the context of a microfluidic device for the analysis, amplification, or other automated manipulation of nucleic acids.

18 Claims, 1 Drawing Sheet

CAPACITIVE DENATURATION OF NUCLEIC ACID

This patent application is related to the following copending U.S. patent applications: Ser. No. 08/556,036, filed Nov. 9, 1995 (now U.S. Pat. No. 5,846,396), entitled A PARTITIONED MICROELECTRONIC DEVICE ARRAY (Zanzucchi et al.); Ser. No. 08/556,423, filed Nov. 9, 1996 (now U.S. Pat. No. 5,858,193), entitled ELECTROKINETIC PUMPING (Zanzucchi et al.); Ser. No. 08/645,966, filed May 10, 1996, entitled ELECTROKINETIC PUMPING (Zanzucchi et al.); Ser. No. 08/483,331, filed Jun. 7, 1995 (now U.S. Pat. No. 5,603,351), entitled METHOD AND SYSTEM FOR INHIBITING CROSS-CONTAMINATION IN FLUIDS OF COMBINATORIAL CHEMISTRY DEVICE (Demers); Ser. No. 08/742,317, filed Nov. 1, 1996 (now U.S. Pat. No. 5,882,903), entitled ASSAY SYSTEM (Roach et al.); Ser. No. 08/745,766, filed Nov. 8, 1996 (now U.S. Pat. No. 5,747,169), entitled FIELD-ASSISTED SEALING (Fan et al.); Ser. No. 08/786, 956, filed Jan. 22, 1997 (now U.S. Pat. No. 5,863,502), entitled PARALLEL REACTION CASSETTE AND ASSOCIATED DEVICES (Southgate et al.); Ser. No. 08/742,971, filed Nov. 1, 1996, entitled MAGNET (McBride); Ser. No. 08/554,887, filed Nov. 9, 1995 (now U.S. Pat. No. 5,842, 106), entitled METHOD OF PRODUCING MICROELECTRONIC CONDUITS (Thaler et al.); Ser. No. 08/664, 780, filed Jun. 14, 1996 (now U.S. Pat. No. 5,863,801), entitled AUTOMATED NUCLEIC ACID ISOLATION (Southgate et al.); Ser. No. 08/730,636, filed Oct. 11, 1996 (now abandoned), entitled LIQUID DISTRIBUTION SYSTEM (Demers et al.); Ser. No. 08/665,209, filed Jun. 14, 1996, entitled MICROFLUIDIC METHOD FOR NUCLEIC ACID AMPLIFICATION (Loewy et al.); Ser. No. 08/665,210, filed Jun. 14, 1996 (now abandoned), entitled METHOD FOR POLYNUCLEOTIDE SEQUENCING (Kumar et al.); Ser. No. 08/665,104, filed Jun. 14, 1996 (now U.S. Pat. No. 5,770,370), entitled NUCLEASE PROTECTION ASSAYS (Kumar); Ser. No. 08/663,688, filed Jun. 14, 1996, entitled METHOD FOR AMPLIFYING A POLYNUCLEOTIDE (Loewy et al.); Ser. No. 08/665,208, filed Jun. 14, 1996, entitled PADLOCK PROBE DETECTION (Kumar); Ser. No. 08/838,102, filed Apr. 15, 1997, entitled METHOD FOR TRANSLOCATING MICROPARTICLES IN A CAPLLARY (Fan et al.); and Attorney Docket No. SAR-12049, filed Jun. 24, 1997, entitled METHOD FOR CAPTURING A NUCLEIC ACID (Loewy et al.).

This invention was made with U.S. Government support under Contract No. N66001-96-C-8630. The U.S. Government has certain rights in this invention.

The present invention relates to the field of nucleic acid analysis, and, in particular, to a method whereby the analyzed or manipulated nucleic acid is denatured as part of such processes by application of an electromagnetic field, such as that provided by capacitive charging.

Nucleic acid in the form of deoxyribonucleic acid (DNA) or ribonucleic acid (RNA) can form stable double-stranded molecules in the familiar double-helical configuration. For typical in vitro studies of such molecules, such as but not limited to those requiring hybridization or amplification procedures, aggressive conditions are required to separate the complementary strands of the double-stranded molecule. Known methods that are used for strand separation typically use high temperatures of at least 60° C., and not uncommonly 100° C., for extended periods of ten minutes or more, which heat is commonly provided by means of a resistance coil either directly applied to the container of the nucleic acid or via a water bath that jackets the container. Such approaches to nucleic acid denaturation suffer from time requirements necessary to reach the required temperature, and a lack of uniformity of temperature shift of the molecules being subjected to the heat. Also, such approaches are inconvenient when the reagent volume is small, as is the case in microfluidic devices, due to evaporation problems. The present invention addresses these and related problems involved in the denaturation of nucleic acids.

SUMMARY OF THE INVENTION

In one embodiment, the invention relates to a method for denaturing a nucleic acid, comprising subjecting a composition comprising the nucleic acid to capacitive charging. The invention further relates to the method wherein the composition is contained in a vessel having an interior surface composed of a dielectric material, a first electrode separated from the composition by the interior surface, thereby defining a capacitor area, and a second electrode insertable into the composition.

In another embodiment, the invention relates to a method for denaturing a nucleic acid in the context of a first chamber that is in communication with one or more second chambers, comprising subjecting a composition comprising the nucleic acid to capacitive charging.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DEFINITIONS

Figure 1:
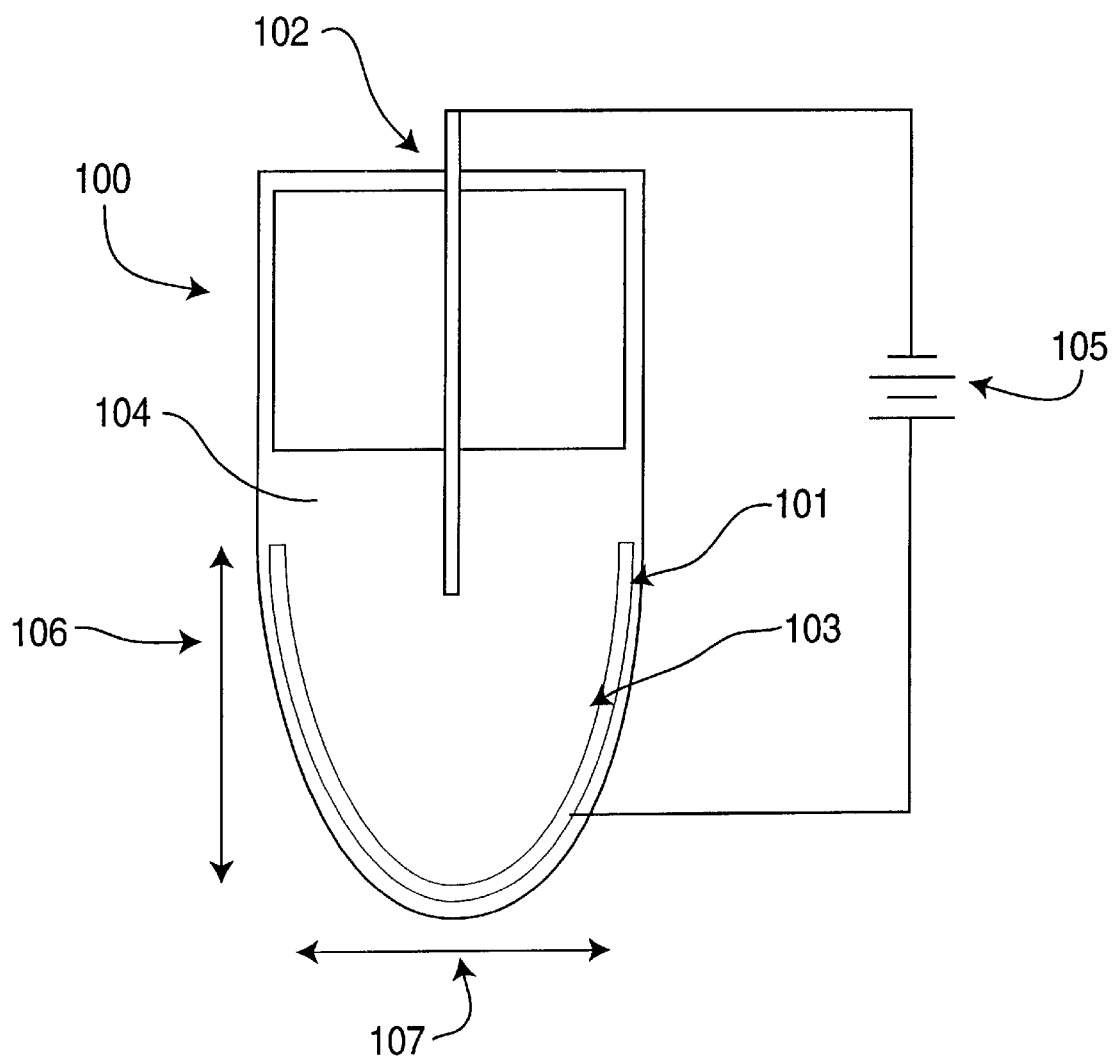
FIG. 1 displays a schematic of a vessel suitable for capacitive charging denaturation.

The following terms shall have, for the purposes of this application, the respective meanings set forth below. In particular, for the purpose of interpreting the claims, the term definitions shall control over any assertion of a contrary meaning based on other text found herein:

"cassette" means a disposable device for conducting reactions therein having a cassette body, one or more upper membranes and one or more lower membranes which together define two or more chambers, including at least one supply chamber and one reaction chamber, and fluid exchange channels connecting the chambers; chambers of a cassette accommodate volumes that range from about 10 µl to about 500 µl.

"chamber" or "fluid chamber" encompasses any reservoir or chamber, including reaction, supply, waste, metering and sample storage chambers, and other fluid-containing chambers; reaction chambers are also referred to herein as "first chambers" and the remaining fluid chambers are also referred to herein as "second chambers". In those embodiments where contents of the chambers can be pumped out using a foot-pad having a shape that conforms to a covering film that is inverted to match the shape of the bottom of the chamber, the chamber can be closed by maintaining the foot-pad pressed against the inverted covering film. Alternatively, particularly in a chip embodiment, the fluid that fills or leaves a chamber is moved via electrodebased pumping.

"channel" or "capillary" means a conduit through which fluids pass between chambers or between a chamber and an inlet or exit of a microfluidic device; also called a "fluid exchange channel".

"chip" means a microfabricated device having chambers and at least one reaction flow way, generally accommodating substantially smaller volumes than does a cassette; for example, chambers of a chip generally accommodate volumes that range from about 250 nl to about 10 $\mu$l.

"connection" or "communication" between two structures selected from chambers, inlets, channels, and capillaries are said to be "connected" or have a "route of connection" or "communicate" or are in "fluid communication" therebetween if there is one or more channels or capillaries joining the two such that fluid can move from one to the other.

"microfluidic device" is a device that comprises a cassette or a chip.

"reaction chamber" means a chamber for locating reactants undergoing or to undergo a reaction, comprised of any suitable material, i.e., a material that exhibits minimal non-specific adsorptivity or is treated to exhibit minimal non-specific adsorptivity, which material can be, for example, glass, plastic, nylon, ceramic, or combinations thereof, and is connected to at least two channels for passaging material in and out of the reaction chamber; also referred to as a "first chamber".

"reaction flow-way" means a series of two or more serially connected chambers through which fluids can move, the connections for which are provided by one or more channels or capillaries.

"serially connected" refers to two or more chambers and inlet or outlet ports that are connected via channels or capillaries by which fluid from a first of the serially connected chambers or ports can pass to a second of the serially connected chambers or ports, and from there to a third of the serially connected chambers or ports, and so on until the fluid passes to the last of the serially connected chambers or ports.

"vessel" means a receptacle in which liquid reagents can be stored or combined, ranging in volume accommodation from milliliters, with respect to wells of a microtiter dish or an Eppendorf tube, for example, 10 to 500 $\mu$l, with respect to fluid chambers included in cassettes, and 250 nl to 10 $\mu$l, with respect to chips.

DETAILED DESCRIPTION OF THE INVENTION

The present invention relates to a method of nucleic acid denaturation that is useful for identification and amplification procedures commonly directed at nucleic acid. In particular, the present invention is intended to be used in the context of an identification or amplification procedure that requires the presence of single-stranded nucleic acid, such as would be required for hybridization with a probe of interest or for amplification. Any nucleic acid hybridization protocol known in the art can be adapted to incorporate the present method of denaturation for allowing a suitable probe to form a duplex molecule with a complementary segment of a given target nucleic acid, such as procedures set forth in, for example, *Short Protocols In Molecular Biology* (Frederick M. Ausubel et al., eds. 1992) (hereinafter, Ausubel et al.). Amplification methods can also be altered to use the present method of nucleic acid denaturation, which methods include, but are not limited to: (1) polymerase chain reaction (PCR; see, e.g., U.S. Pat. No. 4,683,202 and Ausubel et al., Unit 15.1); (2) ligase chain reaction (LCR; see, e.g., European Patent Publication 320,308 and Schachter et al., *J. Clin. Microbiol.*, 32, 2540–2543 (1994)); (3) strand displacement amplification (SDA; see, e.g., Walker et al., *PCR Methods and Applications*, 3, 1–6 (1993)); (4) nucleic acid sequence-based amplification (NASBA; see, e.g., van Gemen et al., *J. Virol. Methods*, 43, 177–188 (1993)); and (5) transcription-mediated amplification (TMA; Pfyffer et al., *J. Clin. Micro.*, 34, 834–841 (1996)). Moreover, the method of the present invention is adaptable for automatable devices useful for manipulating or analyzing nucleic acids, and may be used in the context of microfluidics devices disclosed in the following related U.S. patent applications: Ser. Nos. 08/786,956; 08/742,317; 08/483,331; and 08/730,636, which are incorporated herein by reference. As set forth hereinbelow, the present invention also relates to a device that employs the aforementioned amplification method. Although not necessarily used in the context of a microfluidic device, the method of denaturation disclosed herein is particularly well-suited in such contexts, both with respect to cassettes and chips.

The first two amplification procedures, the PCR and LCR methods, both relate to amplification of DNA segments, and are commonly used in methods of detection and analysis of such segments. These procedures commonly are used with thermal cyclers for generating cycling denaturing-renaturing/reaction temperatures for the reaction. The other two amplification procedures, the SDA and NASBA, also can be used to amplify a DNA segment, but provide RNA amplification products. Typically, these procedures require at least an initial high temperature incubation to provide for the denaturing of the target DNA upon or prior to the adding of primer, after which the reactions are conducted isothermally at a lesser temperature. For example, the NASBA procedure referenced above includes an initial incubation at 75° C. followed by incubations at 41° C. Similarly, the SDA procedure, also referenced above, includes an initial incubation at 95° C. followed by incubations at 37° C. A preferred embodiment of the present method obviates the requirement to have any such fluctuation of temperature, making the inventive procedure more amenable to automation and to the use of relatively less expensive enzymes that need not be thermophilic.

One embodiment of the present invention, namely the capacitive charging method of denaturation, contemplates an adaptation of the aforementioned amplification methods to accommodate a fully isothermal method with respect to both denaturation and ligation or polymerization. In addition to the capacitive charging denaturation more fully described below, the fully isothermal embodiment of the present invention includes chemical means for ligating two abutting oligonucleotides. Such methods include use of cyanogen bromide or carbodiimide, for example, which are used in accordance with conventional procedures. See, for example, Rubin et al., *Nucleic Acids Res.*, 23, 3547–3553 (1995); and Ng and Orgel, *Nucleic Acids Res.*, 15, 3573–3580 (1987).

As a general rule, the present method requires that the temperature of the reactants of an amplification or hybridization procedure be maintained at certain levels for the effective and efficient use of certain enzymes used in the amplification procedure or for the fostering of the hybridization process; in some embodiments, the method performs effectively at ambient room temperature, such as between about 20° C. and about 30° C. Other embodiments require the temperature of the reactants to be higher, say up to about 75° C. However, in contrast to the methods described above, one embodiment of the method set forth herein is fully effective under isothermic conditions, albeit other embodiments operate using alternating temperatures, or an initial temperature at one level followed by incubation for the remainder of the procedure at a second level.

In one embodiment, nucleic acid is denatured via application of capacitive charging of the composition in which the nucleic acid is situated. Such a procedure can be understood by understanding that the nucleic acid double helix, whether DNA:DNA, RNA:RNA, or DNA:RNA, is an entropically disfavored configuration that is stabilized by interaction of the highly negatively charged double-stranded nucleic acid backbone with salt ions, wherein positive charges are referred to as "counterions" and negative charges are referred to as "coions". Low ionic strength in a double-stranded nucleic acid solution tends to destabilize the double-stranded nucleic acid helix. In a buffer with ionic strength 0.01 M, double-stranded nucleic acid is stable, but when this ionic strength is reduced to 0.0001 M the double-stranded nucleic acid has a tendency to denature. The process of capacitive charging serves to reversibly reduce the number of counterions from the vicinity of the double-stranded nucleic acid.

The method of capacitive charging involves making the composition that includes the nucleic acid one plate of a capacitor. As the capacitor voltage is increased, the buffer of the composition absorbs charge and changes pH. An example of a vessel 100 in which capacitive charging can occur is presented in FIG. 1. The vessel 100 includes a first electrode 101 and a second electrode 102, wherein the first electrode is coated with an insulating film 103 composed of a dielectric material so that the first electrode cannot come into direct contact with the nucleic acid composition 104 and the second electrode 102 is reversibly inserted into the nucleic acid composition 104. As long as suitable electrochemistry can facilitate charge transfer at the immersed second electrode 102, which is accomplished by connecting the first and second electrodes 101 and 102 to a suitable source of electrical potential, such as a battery 105, then the capacitance of the insulating film 103 dominates the electrical response and causes denaturation of the double-stranded nucleic acid included in the composition 104.

The Debye length, which is a measure of the distance through a solution that an electric field will penetrate, is inversely proportional to the square root of the salt concentration. It is important to note that the Debye length of a 0.01 M salt solution is about 1 nm. Accordingly, the screening of the electric field that occurs through reorganization of the solution charges renders the field ineffective over distances greater than 1 nm. Thus, the only way to significantly lower the ionic strength in the bulk solution is to remove some of the charges through electrochemistry. An appropriate electrochemical reaction over a large surface area surrounding a small volume of nucleic acid solution is sufficient to significantly alter the ionic strength in the vicinity of the nucleic acid.

Amphoteric molecules can also be used to produce pH changes controlled by an electric field. Amphoteric molecules are highly charged molecules with multiple positive and negative charge states. On application of an electric field, these molecules drift in solution until they enter a region with a pH at which they are neutral. By selecting suitable groups of amphoteric molecules, such as, but not limited to, Ampholines® (Pharmacia LKB Biotechnology AB), Sigma Ampholytes (Sigma Chemical Company, St. Louis), Immobiline® (Pharmacia), or Pharmalytes® (Pharmacia), one can create regions of varying and precisely controlled pH produced by application of an electric field. Varying the electric field allows successive regions of an aqueous DNA solution, such as the aforementioned composition, to denature by becoming more alkaline.

In particular, the present invention in one embodiment pertains to a method for denaturing a nucleic acid, comprising subjecting a composition comprising the nucleic acid to capacitive charging. The nucleic acid can be RNA or DNA, and the denaturation referred to is the "melting" of double-stranded to single-stranded forms of either homo- or heteroduplexes of the RNA and DNA. The composition in which the nucleic acid is dissolved or suspended is further comprised of any suitable solvent, such as an aqueous buffer, which is preferably a phosphate or Tris buffer or the like. The capacitive charging method is preferably applied to the composition contained in a suitable vessel having an interior surface composed of a suitable dielectric material, a first electrode separated from the composition by the interior surface, thereby defining a capacitor area, and a second electrode insertable into the composition. The first and second electrodes can be composed of any suitable conductive material, such as but not limited to copper, platinum, and the like. A suitable dielectric material of the interior surface preferably has a dielectric constant of from about 2 to about 20, more preferably from about 5 to about 15, yet more preferably from about 7 to about 12.

In a preferred embodiment, the first or second electrode is reversibly connected to a source of electrical potential or the first and second electrodes are connected to a source of electrical potential and the second electrode is reversibly in contact with the composition. The source of electrical potential can be a battery or a standard house current line transformed to a suitable potential, either providing preferably from about 10 to about 1500 volts direct current, more preferably from about 50 to about 1200 volts direct current, yet more preferably from about 500 to about 1000 volts direct current. The reversible connection of the first or second electrode to the source of electrical potential can be effected by any standard electrical switch, such as a standard toggle switch, a timed switch that provides for periodic completion and opening of the circuit, or a switch connected to a thermostat that opens or closes the switch in consequence of temperature of the first chamber, for example. The reversible contact between the second electrode and the composition can be effected by mechanically moving the electrode out of contact with the composition and thereafter inserting the second electrode therein. Such mechanical movements can be mediated by mechanisms known in the art. The first and second electrodes, wherein the second electrode is in contact with the composition, are preferably connected to the source of electricity for intervals of from about 0.1 to about 120 seconds, more preferably from about 0.5 to about 90 seconds, yet more preferably from about 1 to about 60 seconds.

The composition that includes the nucleic acid preferably has ionic strength preferably of from about 0.5 M to about 0.0001 M, which is provided by varying the included salt of the included buffer, or adding additional salt beyond the requirements of the buffer. More preferably, the ionic strength of the composition is of from about 0.2 M to about 0.0005 M, yet more preferably, from about 0.1 M to about 0.001 M. Most preferably, the composition has ionic strength of from about 0.015 M to about 0.005 M. In a preferred embodiment, the nucleic acid composition further comprises amphoteric species, such as, but not limited to, Ampholines® (Pharmacia LKB Biotechnology AB), Sigma Ampholytes (Sigma Chemical Company, St. Louis), Immobiline® (Pharmacia), or Pharmalytes® (Pharmacia).

The nucleic acid composition also preferably comprises an enzyme for which the nucleic acid is a substrate. Suitable enzymes are those that are used in the context of the aforementioned hybridization or amplification procedures, such as, but not limited to, DNA polymerase, RNA polymerase, DNA-dependent reverse transcriptase, ligase, and the like. As used herein, the term polymerase can be used without further modification and refers to the enzyme used to amplify or extend RNA, in which case the substrate is RNA and the enzyme is RNA polymerase, or DNA, in which case the substrate is DNA and the enzyme is DNA polymerase. Preferably, the enzyme used in the context of the present invention is a polymerase or a ligase.

The capacitor area defined by the first and second electrodes in combination with the nucleic acid composition is preferably from about $1\times10^{-4}$ to about $5\times10^{-4}$ square meters ($m^2$), more preferably from about $1\times10^{-5}$ to about $5\times10^{-5}$ $m^2$, yet more preferably from about $1\times10^{-6}$ to about $5\times10^{-6}$ $m^2$. The first and second electrodes preferably have a capacitance of from about 0.1 to about 50 nF, more preferably from about 0.5 to about 25 nF, yet more preferably from about 1 to about 5 nF, and even more preferably from about 2 to about 4 nF.

Figure 2:
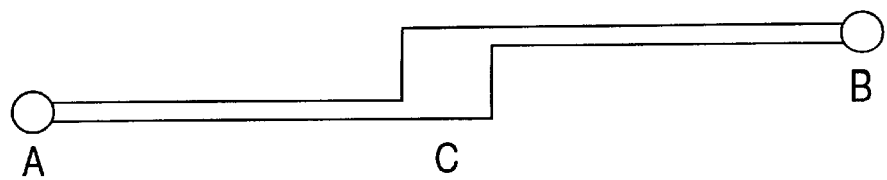
FIG. 2 displays a generic microfluidic device.

In a second embodiment of the present invention, the method for denaturation of the nucleic acid occurs in the context of a first chamber that is in communication with one or more second chambers, comprising subjecting a composition comprising the nucleic acid to (a) capacitive charging. The first chamber and serially connected other first chambers or second chambers or parallel such first and second chambers are preferably included in a standardized miniaturized (referred to as a "cassette") or microfabricated (referred to as a "chip") structure that is comprised of the aforementioned chambers and channels, as described in Ser. Nos. 08/742,317 and 08/664,780 with respect to the cassette, and Ser. Nos. 08/483,331 and 08/554,887 with respect to the chip. A representation of such a structure is provided by FIG. 2, wherein A and B represent second chambers, C represents a first chamber, and the narrow lanes that respectively connect A and B to C are fluid exchange channels. Each type of chamber and the channels are further defined below.

The present invention can be practiced in the context of either a cassette or a chip, the essential difference between the two being the quantity of sample and reagents used, and the sizes of the channels and reservoirs included therein. In certain embodiments, a reservoir functions as a reaction site, referred to herein as a "first chamber". A reservoir can also function as a storage site for reagents or a waste receptacle, each of which reservoirs are referred to herein as a "second chamber". In certain embodiments, a particular chamber can function as a site for a reaction, thus be a first chamber, yet in another stage of the method as thus embodied, the same chamber can function as a waste receptacle, thus be a second chamber.

The reservoirs used in a cassette or chip are one or more first chambers, in which reactions relating to the identification method can take place, although the same reactions can also take place in second chambers or channels, depending on the design used in a particular embodiment. The cassette or chip used in the context of the present invention also includes at least one second chamber, which contain reagents used in the identification method, or are used as a receptacle for waste that results from the identification method. Again, the same second chamber that initially was a storage facility for reagents at a prior stage of the method can serve as a waste receptacle, or as a reaction chamber, or both at varying times. Simply put, the cassette and chip design provides much latitude for design variations for placement of first or second chambers and interconnecting fluid exchange channels. Valves, both of a reversible and irreversible sort, can be used in this context, including chambers that provide their own irreversible "valve." See Ser. Nos. 08/742,317 and 08/664,780.

More particularly with respect to the cassette used in the context of the present invention, the cassette itself can be made of any suitable material having characteristics of sufficient moldability for forming the cassette, sufficient strength and resistance to chemical attack, and the like; for example, the cassette is preferably formed of a molded plastic, such as high density polyethylene, but other materials that are suitably resistant to the chemistries used in nucleic acid identification, such as glass and silicon-based materials, can be used. Where the cassette is formed of plastic, it is preferably formed by a molding process that is used to form cavities and channels that will be sealed with upper and lower plastic films to form second chambers and fluid exchange channels. Such cavities and channels are formed in suitable materials, such as glass and silicon materials, by chemical etching or laser ablation. Upper and lower films typically have a thickness of from about 0.3 mils to about 5 mils, preferably from about 1 mil to about 3 mils. For chambers having a diameter of about 1 cm or more, the film thickness is more preferably about 2 mils. The first chamber, in which the reactions relating to the nucleic acid preparation take place, typically has a thickness, between the upper and lower films, of from about 0.1 mm to about 3 mm, preferably of from about 0.5 to about 1.0 mm, and an area, defined by the inner surface of the upper or lower films, of preferably from about 0.05 $cm^2$ to about 2 $cm^2$, more preferably from about 0.1 $cm^2$ to about 1 $cm^2$, yet more preferably about 0.5 $cm^2$. The dimensions of the first chamber are preferably sized small enough to permit rapid throughput of fluids so that the chemical conditions of the substrates having probe moieties or first nucleic acid, depending on the embodiment being practiced, attached thereto can be exchanged predictably and rapidly (on the order of about one to about 10 seconds). Preferably, the total volume of each first chamber in a cassette is between about 5 $\mu l$ and about 250 $\mu l$, more preferably, between about 10 $\mu l$ and about 100 $\mu l$. Preferably, each first chamber has a thickness (i.e., distance between upper film and lower film) of about 1 mm or less.

Fluid exchange channels in a cassette typically describe a cylinder and have a diameter between about 200 $\mu m$ and about 500 $\mu m$; alternatively, the channels can be constructed in other shapes having a width or depth respectively of from about 200 $\mu m$ to about 500 $\mu m$. Second chambers typically have a volume capacity between about 5 $\mu l$ and about 500 $\mu l$, preferably from about 10 $\mu l$ to about 200 $\mu l$, more preferably from about 30 $\mu l$ to about 160 $\mu l$. The second chambers can contain reagents required in the identification of the nucleic acid, such as hybridization reagent, wash fluid, microparticles, Tris-EDTA (TE) buffer, and the like; such reagents can be contained in the second chambers in dry or liquid form, and if in dry form, can be constituted with water or other liquid reagent contained in other second chambers, or from water or other liquid reagent delivered from an external source. Second chambers used for metering a given volume preferably have a volume between about 5 µl and about 50 µl.

The upper and lower films preferably are resistant to temperatures at least as high as about 120° C. and are between about 0.5 and about 4 mils in thickness, more preferably, between about 1 and about 3 mils. The thinness of the membranes facilitates rapid heat exchange between the first chamber, or wherever the reactions to be effected within the cassette are to be located, and an adjacent heating or cooling device, which can be used to establish a constant temperature for the sample of nucleic acid being tested, if desired.

The cassette comprising the aforementioned first chambers, second chambers, including supply, waste, and metering chambers, fluid exchange channels, and the valves and pumps further discussed previously (see Ser. No. 08/664,780), can have any suitable design. Indeed, any cassette design that includes at least one second chamber, at least one first chamber, and means of communication therebetween (i.e., the fluid exchange channels) suitable for the identification of a first nucleic acid is preferred. More preferred, the cassette comprises up to six wells for entry of a sample container and its contents, which are connected to one or more first chambers into which the first nucleic acid is distributed, and where the first nucleic acid is contacted by probe moieties stored in second chambers, which probe moieties are second nucleic acids that are specific for different target nucleic acids or segments thereof that may be contained within the mixture of nucleic acids combinedly referred to as the first nucleic acid. Alternative probe moieties set forth herein are DNA binding proteins, as discussed above.

Alternatively, the microfabricated device, i.e., the chip, used in the context of the present invention preferably includes channels filled with fluid, wherein the channels are preferably less than about 300 µm wide and less than about 300 µm deep. The microfabricated device can be constructed of any suitable material or combination of materials, including but not limited to a glass, plastic, and the like, wherein a suitable material is substantially rigid at room temperature (about 25° C.) up to at least about 40° C., and remains a solid at a temperature of up to at least about 120° C. In addition to the channels included in the microfabricated device, a preferable device comprises reservoirs, including a first chamber and one or more second chambers that are interconnected by the channels. The first chamber is alternatively referred to as the reaction chamber, however, one of the advantages of the present method is the ability to use any chamber or any channel or portions thereof as the site of the reactions needed for the diagnostic procedure, as further discussed below. The second chambers are alternatively referred to as supply or waste chambers. The aforementioned material from which the chip is constructed can vary at or about the chambers, such as, for example, including at least one deformable wall at a chamber, preferably a second chamber. Preferably, the chip has at least two second chambers that have a deformable wall.

The first chamber of a chip preferably has dimensions of from about 25 µm to about 10 µm wide, from about 25 µm to about 10 µm long, and from about 5 µm to about 500 µm deep. More preferably, the first chamber has dimensions of from about 50 µm to about 5 µm wide, from about 50 µm to about 5 µm long, and from about 10 µm to about 300 µm deep. Yet more preferably, the first chamber has dimensions of from about 100 µm to about 1 mm wide, from about 100 µm to about 1 mm long, and from about 20 µm to about 100 µm deep. The volume capacity of the first chamber of a chip is preferably from about 100 picoliters to about 10 µl; more preferably, from about 1 nl to about 5 µl; yet more preferably from about 10 nl to about 1 µl.

The second chambers have any suitable dimensions such that sufficient reagents and waste chambers are thereby provided in the chip for the nucleic acid identification protocol for which the chip is designed. In most applications, volume requirements of the second chambers preferably will not exceed about 500 µl; more particularly, second chambers used for waste disposal preferably have a volume capacity of from about 200 µl to about 500 µl, whereas second chambers used for reagent storage preferably have a volume capacity of from about 50 µl to about 250 µl.

The channels included in the chip preferably have dimensions of from about 5 µm to about 500 µm wide, from about 5 µm to about 500 µm deep, and from about 500 µm to about 250 µm long. More preferably, the channels included in the chip preferably have dimensions of from about 15 µm to about 300 µm wide, from about 10 µm to about 300 µm deep, and from about 1 mm to about 100 mm long. Most preferably, the channels have dimensions of from about 30 µm to about 150 µm wide, from about 20 µm to about 100 µm deep, and from about 1 mm to about 50 mm long. The channels can be situated colinear or not colinear with respect to the first chamber. For example, for one embodiment that has a colinear arrangement of channels and chambers, all of the channels and chambers would be aligned in the same plane as one that is parallel with the wall of the chip. In contrast, an alternative embodiment that has a non-colinear arrangement can have a chamber situated adjacent to one wall of the chip and all or some of the channels situated adjacent to the other wall of the chip, i.e., the channels or some of the channels are situated in different planes than is at least one of the chambers. In such an embodiment, the channel would connect to a chamber by a bend away from a parallel plane with the adjacent wall, bending toward the chamber. Alternatively, channels connected to a chamber can interface the chamber such that one channel can be connected to opposite corners of, for example, a square or cube shaped chamber.

As can be appreciated from the above discussion concerning the preferred components and dimensions of cassettes and chips, which collectively are referred to herein as "structures," in one embodiment, the present method is suitably conducted in either context. The structure is referred to herein as a removable chemistry cassette or a microfabricated device, one of the distinguishing features of which are the range of sizes of the included chambers and fluid exchange channels. For example, whereas the generic structure preferably includes a first chamber having a volume of from about 0.05 µl to about 250 µl, the first chamber of a chip preferably has a volume of from about 0.1 µl to about 10 µl and that of a removable cassette has a volume of from about 10 µl to about 100 µl.

The composition that includes the nucleic acid preferably includes a microparticle. A microparticle can have any shape, which is preferably spherical and when spherical, it is referred to as a "bead." Preferably, the microparticle has no dimension in excess of about 500 µm; and more preferably, of less than about 100 µl. In certain preferred embodiments, the microparticles have a maximum dimension of from about 0.5 µm to about 25 µm, and more preferably from about 1 µm to about 5 µm, and even more preferably, about 2 µm to about 4 µm. Accordingly, beads used in the context of the present invention have diameters in accordance with the aforementioned maximum dimensions. Microparticles are comprised of any suitable material, the choice of material being guided by its characteristics, which preferably include minimal non-specific adsorptive characteristics with respect particularly to proteins or nucleic acids, such as that of polystyrene. In other embodiments, the microparticles are comprised of, for example, glass, cellulose or a cellulose derivative, plastic, such as nylon or polytetrafluoroethylene ("TEFLON"), metal, ceramic and the like, and combinations thereof.

A preferred microparticle used in the context of the present invention is magnetic. More preferably, the microparticle is paramagnetic. A paramagnetic microparticle can be comprised of, for example, iron dispersed in a polystyrene matrix, and can be obtained, for example, from Dynal (Oslo, Norway). Yet more preferably, the microparticle is superparamagnetic, where the distinction between paramagnetic and superparamagnetic microparticles is that the former retain some magnetic attraction after a magnetic field has been removed and thus tend to clump or remain clumped, whereas the latter have no remanence in the absence of the magnetic field and thus are readily dispersed after a magnetic field is removed.

The preferred microparticle has a moiety attached thereto. A suitable moiety includes a means for binding the microparticle to defined molecules, such as a probe that preferentially binds to a target nucleic acid, more preferably to a particular segment included in the target nucleic acid, which moiety is referred to herein as a probe moiety. A probe is a molecule that preferentially binds to a particular sequence of a nucleic acid, such as an oligonucleotide that under appropriate conditions hybridizes to a nucleic acid that includes a segment that is complementary to at least a portion of the oligonucleotide. Other exemplary probes are discussed below. An alternative moiety includes a means for signalling the presence of the microparticle, which alternative moiety is referred to herein as an indicator moiety. The moiety can also be a chemical species that preferentially or, yet more preferably, exclusively binds to a second chemical species, for the purpose of attaching, for example, an indicator or probe moiety to the substrate. A moiety that so binds to the second chemical species is herein referred to as a binding moiety, which can be, but is not limited to, avidin, biotin, streptavidin, fluorenylmethoxycarbonyl (FMOC), an antibody, Protein A, or a lectin.

Overall, any aforementioned embodiment of the moiety comprises an organic or inorganic compound. Preferably, such a compound comprises an amino acid, a polypeptide, a nucleotide, a nucleoside, a nucleic acid, a carbohydrate, or an organic compound, or a combination thereof, such that it is a probe, an indicator, or a chemical species that preferentially or exclusively binds to a second chemical species.

Preferably, the probe or indicator attaches to the microparticle by means of a covalent linkage. Such a linkage can be direct between the probe or indicator to a component of the microparticle. Alternatively, the linkage can be indirect by means of a binding moiety as set forth above. A preferred embodiment of such an indirect means comprises the covalent attachment to the microparticle of a binding moiety that preferentially or, more preferably, exclusively binds to a second chemical species that is covalently attached to the probe or indicator moiety. For example, avidin can be attached to the microparticle and biotin can be attached to the probe or indicator; the combining of the so-constructed microparticle and probe or indicator will result in linked microparticle and probe or indicator, possibly both, using procedures well known in the art.

As noted above, the microparticle can include an indicator moiety; the nucleic acids that are targets of hybridization or amplification or other manipulation that involves a denaturation step as provided by the present invention can also include an indicator moiety. In the context of the present invention, the indicator moiety can be attached to the nucleic acids of the population, or to the microparticle or probe or any other substrate, such as an interior surface of the microfluidic device, or to the target nucleic acids and the microparticle or probe, or to all three. Thus, the target nucleic acids, probe or substrate includes an indicator moiety, provided that distinguishable indicator moieties are used when at least two of the target nucleic acids, probe, and substrate include an indicator moiety. Preferably, the indicator moiety is fluorescent, radioactive, or a substance that causes a color or light change, embodiments of which are well known in the art. Distinguishable indicator moieties used in the context of the present invention can be any combination of the aforementioned indicator moieties, including radioactive indicators, e.g., radioactive isotopes of phosphorus, carbon, hydrogen, sulfur, and the like, fluorescent indicators, e.g., rhodamine, fluoroscine, and the like, and enzymes that cause a color or light change under appropriate conditions and in the presence of appropriate substrates, e.g., alkaline phosphatase, luciferase, and the like. By "distinguishable" it is intended that different indicator moieties can be used to identify those nucleic acids captured by one probe moiety versus another, as in having a radioactive hydrogen included in an indicator moiety that is attached to a first probe moiety complexed to one target nucleic acid; which can be distinguished from a second probe moiety complexed to a different target nucleic acid if the second probe moiety includes, for example, a radioactive carbon or a fluorescent tag, such as rhodamine or fluoroscine.

Detecting the presence of a target nucleic acid, wherein the target nucleic acid has attached to the probe thereby forming a complex, comprises exposing a suitable detector to the complex, wherein the detector is a detector of radiation, fluorescence, or light, which are known in the art.

With respect to the embodiment of the present invention that includes practice of the capacitive charging denaturation in the context of a microfluidic device, as defined as a first chamber in communication with one or more second chambers, all of the features of the (a) vessel, (b) characteristics of the composition with respect to electrolyte concentration, inclusion of ampholytes or zwitterions, enzymes, etc., (c) reversibility of connection of the electrodes to the source of electrical potential, (d) reversibility of the contact between the second electrode and the composition, characteristics of the dielectric material, (e) capacitor area, (f) capacitance, (g) use of DNA or RNA, (h) and length of connection to the source of electrical potential, each of which are noted above in the discussion of the capacitive charging embodiment per se, are applicable to either a first or second chamber or a channel or capillary of the microfluidic device. The vessel recited with respect to the capacitive charging aspect of the present invention is defined herein so as to included a first or second chamber, which is the term appropriately used in the context of the microfluidic device. Further, the site of the denaturation could be any internal portion of the microfluidic device, such as, without limitation, a channel or capillary. A first electrode, accordingly, can be fixed to the internal portion of any or each of the aforementioned components of a microfluidics device and covered by a suitable dielectric material, for example; alternatively, the second electrode can be fixed to the outside surface of any or each of the identified components. In all respects, one skilled in the art will appreciate that the same features discussed hereinabove with regard to the capacitive charging denaturation are amenable to use in the context of a microfluidics device as described herein.

The following examples further illustrate the present invention, but of course, should not be construed as in any way limiting its scope.

EXAMPLE 1

This example illustrates a feasibility study of capacitive charging denaturation of nucleic acid according to the invention.

Using a vessel 100 as set forth in FIG. 1, wherein the vertical dimension 106 and horizontal dimension 107 of the portion of the vessel 100 in contact with the first electrode 101 are each about 1 mm, a feasibility study of capacitive charging denaturation can be set forth. For this study, the insulating film 101 is 0.1 $\mu$m thick and has a dielectric constant of 10 and a capacitor area of $3 \times 10^{-6}$ m$^2$; accordingly, the first and second electrodes 101 and 102 can have a capacitance of 3 nF. Upon application of 1000 V to the first and second electrodes 101 and 102, which are the positive and negative electrodes, respectively, the charge added to the solution is $3 \times 10^{-6}$ C, or about $2 \times 10^{13}$ charges. When the ionic strength of the composition buffer is 0.01 M with a volume of 1 $\mu$l, the composition has a total of about $6 \times 10^{15}$ charges, which is sufficient for the denaturation event.

EXAMPLE 2

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method for denaturing a nucleic acid in a composition contained in a vessel having an interior surface composed of a dielectric material, comprising:

subjecting the composition to capacitive charging by applying voltage across a first electrode separated from the composition by the interior surface, thereby defining a capacitor area, and a second electrode inserted into the composition; and thereby denaturing the nucleic acid.

2. The method of claim 1, wherein (a) the first or second electrode is reversibly connected to a source of electrical potential or (b) the first and second electrodes are connected to a source of electrical potential and the second electrode is reversibly in contact with the composition.

3. The method of claim 2, wherein the dielectric material of the interior surface has a dielectric constant of from about 5 to about 15.

4. The method of claim 3, wherein the capacitor area is from about $1 \times 10^{-6}$ to about $5 \times 10^{-6}$ square meters (m$^2$).

5. The method of claim 4, wherein electrodes have a capacitance of from about 1 to about 5 nF.

6. The method of claim 1, wherein the composition has ionic strength of from about 0.1 M to about 0.001 M.

7. The method of claim 6, wherein the composition has ionic strength of from about 0.015 M to about 0.005 M.

8. The method of claim 1, wherein the composition includes amphoteric species in an amount effective to alter pH changes caused by applying a voltage across the electrodes.

9. The method of claim 1, wherein the composition further comprises an enzyme for which the nucleic acid is a substrate.

10. The method of claim 10, wherein the nucleic acid is DNA or RNA.

11. The method of claim 11, wherein the enzyme is a ligase or a polymerase.

12. The method of claim 1, wherein the first and second electrodes are connected to the source of electricity with the second electrode inserted into the composition for intervals of from about 1 to about 60 seconds.

13. A method for denaturing a nucleic acid in a composition in a first chamber (i) having an interior surface composed of a dielectric material and (ii) that is in communication with one or more second chambers, the method comprising;

subjecting a composition comprising the nucleic acid to capacitive charging by applying voltage across a first electrode separated from the composition by the interior surface, thereby defining a capacitor area, and a second electrode inserted into the composition; and thereby denaturing the nucleic acid.

14. The method of claim 13, wherein the first chamber has a volume of from about 0.05 $\mu$l to about 250 $\mu$l.

15. The method of claim 13, wherein the composition further comprises a particle having diameter of 500 $\mu$m or less.

16. The method of claim 15, wherein the particle is paramagnetic or superparamagnetic.

17. The method of claim 13, wherein the composition further comprises an enzyme for which the nucleic acid is a substrate.

18. The method of claim 17, wherein the nucleic acid is DNA or RNA.

* * * * *

UNITED STATES PATENT AND TRADEMARK OFFICE
CERTIFICATE OF CORRECTION

PATENT NO : 5,993,611
DATED : November 30, 1999
INVENTOR(S): Giampietro PIRO, et al.

It is certified that an error appears in the above-identified patent and that said Letters Patent is hereby corrected as shown below:

On the title page, item [73] should read:

-- [73] Assignee. Eniricerche S.p.A., San Donato Milanese, Italy --

--[30]      Foreign Application Priority Data

Aug. 4, 1995    [IT]    Italy ............................................. MI95A 001729 --

Signed and Sealed this

Twenty-fourth Day of April, 2001

Attest:

NICHOLAS P. GODICI

*Attesting Officer*      *Acting Director of the United States Patent and Trademark Office*